(12) United States Patent
Tang et al.

(10) Patent No.: US 10,939,883 B2
(45) Date of Patent: Mar. 9, 2021

(54) LIFTING APPARATUS AND A RADIATION SYSTEM INCLUDING THE SAME

(71) Applicant: SHANGHAI UNITED IMAGING HEALTHCARE CO., LTD., Shanghai (CN)

(72) Inventors: Yang Tang, Shanghai (CN); Xuegang Zhong, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 16/504,421

(22) Filed: Jul. 8, 2019

(65) Prior Publication Data

US 2020/0187885 A1    Jun. 18, 2020

(30) Foreign Application Priority Data

Dec. 18, 2018 (CN) .......................... 201811550675.8

(51) Int. Cl.
*A61B 6/00* (2006.01)
*A61B 90/50* (2016.01)

(52) U.S. Cl.
CPC ............ *A61B 6/4405* (2013.01); *A61B 6/447* (2013.01); *A61B 6/4458* (2013.01); *A61B 6/4476* (2013.01); *A61B 6/54* (2013.01); *A61B 90/50* (2016.02)

(58) Field of Classification Search
CPC ...................................................... A61B 6/44
See application file for complete search history.

(56) References Cited

U.S. PATENT DOCUMENTS

| | | | | |
|---|---|---|---|---|
| 2,168,209 A | * | 8/1939 | Haupt | A61B 6/447 248/572 |
| 2,798,958 A | * | 7/1957 | Hudson | A61B 6/4476 378/39 |
| 2,876,362 A | * | 3/1959 | Foderaro | F16M 13/027 378/194 |
| 8,568,028 B2 | * | 10/2013 | Wendlandt | A61B 6/447 378/198 |

(Continued)

FOREIGN PATENT DOCUMENTS

| | | |
|---|---|---|
| CN | 101744626 A | 6/2010 |
| CN | 205503859 U | 8/2016 |

(Continued)

*Primary Examiner* — Thomas R Artman
(74) *Attorney, Agent, or Firm* — Metis IP LLC

(57) ABSTRACT

The present disclosure relates to a lifting apparatus. The lifting apparatus may include a base column, a mobile column, a sliding component, a supporting arm, a lifting system, and a move-coordination system. The mobile column connected to the base column may be vertically movable relative to the base column. The lifting system may be configured to cause the movement of the mobile column. The sliding component connected to the mobile column may be vertically movable relative to the mobile column. The mobile column and the sliding component may be connected via the move-coordination system, which enables the sliding component and the mobile column to move simultaneously according to a predetermined relative motion relationship. The supporting arm may be connected to the sliding component.

21 Claims, 11 Drawing Sheets

(56) References Cited

U.S. PATENT DOCUMENTS

| | | | |
|---|---|---|---|
| 8,876,379 B2* | 11/2014 | DiRisio | A61B 6/447 |
| | | | 378/198 |
| 9,521,984 B2 | 12/2016 | Moreno Vallejo et al. | |
| 10,575,813 B2* | 3/2020 | Takemoto | A61B 6/4405 |
| 2011/0249804 A1* | 10/2011 | Wendlandt | A61B 6/447 |
| | | | 378/198 |
| 2011/0249805 A1 | 10/2011 | Kralles et al. | |
| 2011/0249806 A1* | 10/2011 | Wendlandt | A61B 6/4405 |
| | | | 378/198 |
| 2011/0249807 A1* | 10/2011 | Dirisio | A61B 6/447 |
| | | | 378/198 |
| 2019/0069860 A1 | 3/2019 | Takemoto et al. | |
| 2019/0069872 A1* | 3/2019 | Takemoto | H05G 1/02 |
| 2019/0357863 A1* | 11/2019 | Dirisio | A61B 6/447 |
| 2020/0187885 A1* | 6/2020 | Tang | F16M 3/00 |
| 2020/0229779 A1* | 7/2020 | Takemoto | A61B 6/4452 |

FOREIGN PATENT DOCUMENTS

| | | |
|---|---|---|
| CN | 106388844 A | 2/2017 |
| CN | 108523910 A | 9/2018 |
| JP | H04122243 A | 4/1992 |

\* cited by examiner

LIFTING APPARATUS AND A RADIATION SYSTEM INCLUDING THE SAME

CROSS-REFERENCE TO RELATED APPLICATIONS

This application claims priority of Chinese Patent Application No. 201811550675.8 filed on Dec. 18, 2018, the entire contents of which are hereby incorporated by reference.

TECHNICAL FIELD

This present disclosure relates to a lifting apparatus, and in particular to a lifting apparatus integrated into a radiation apparatus.

BACKGROUND

Mobile radiation apparatus (such as mobile X-ray apparatus, mobile gamma ray appliances) have special application value in an operating room, an intensive care unit, or other scenarios where a patient has impaired physical mobility and a radiation imaging/therapy is needed. A lifting apparatus is usually part of the mobile radiation apparatus to support and move a radiation emitting component (e.g., an X-ray emitter) with respect to the body of the mobile radiation apparatus, so that the radiation emitting component will not block the sight of the operator who is moving the mobile radiation apparatus, thereby avoiding collisions and accidents.

Moreover, the lifting apparatus also helps the radiation emitting component to emit radiation rays to the patient in a proper angle and/or position. That is to say, a properly designed lifting apparatus with an enlarged movement range of the radiation component is able to facilitate the imaging/therapy process as well as the movement of the mobile radiation apparatus. Therefore, it is desirable to provide a lifting apparatus that provides a relatively large movement range for the radiation component of a mobile radiation apparatus.

SUMMARY

According to an aspect of the present disclosure, a lifting apparatus is provided. The lifting apparatus may include a base column, a mobile column, a sliding component, a supporting arm, a lifting system, and a move-coordination system. The mobile column connected to the base column may be vertically movable relative to the base column. The lifting system may be configured to cause the movement of the mobile column. The sliding component connected to the mobile column may be vertically movable relative to the mobile column. The mobile column and the sliding component may be connected via the move-coordination system, which enables the sliding component and the mobile column to move simultaneously according to a predetermined relative motion relationship. The supporting arm may be connected to the sliding component.

In some embodiments, the predetermined relative motion relationship may include the sliding component moving relative to the base column and the mobile column moving relative to the sliding component both along a same direction. A moving distance of the sliding component relative to the mobile column may be proportional to a moving distance of the mobile column relative to the base column.

In some embodiments, the move-coordination system may include a first pulley and a first cable coiled around the first pulley. A first end of the first cable may be connected to the base column. A rotating shaft of the first pulley may be connected to the mobile column. A second end of the first cable is connected to the sliding component through the first pulley.

In some embodiments, the first pulley may be a single radii-pulley or a two-radii pulley having a first radius and a second radius.

In some embodiments, a ratio of the first radius to the second radius may be equal to a ratio of a vertical movement distance of the mobile column relative to the base column to a vertical movement distance of the sliding component relative to the mobile column.

In some embodiments, the lifting system may be configured to cause the mobile column to move relative to the base column according to a predetermined moving manner.

In some embodiments, the lifting apparatus may further include a first motor connected to and drive the move-coordination system.

In some embodiments, the lifting apparatus may further include a first controller in communication with the first motor. The first controller may be configured to cause the first motor to move the sliding component to a predetermined position.

In some embodiments, the lifting apparatus may further include a locking mechanism having a first state and a second state. In the first state, the locking mechanism may unlock at least one element of the move-coordination system or the lifting system to enable the sliding component to move. In the second state, the locking mechanism may lock the at least one element of the move-coordination system or at least one element of the lifting system to stop/disable the sliding component from moving.

In some embodiments, the lifting system may include a cone pulley, at least one movable pulley, a spring and a second cable. A rotating shaft of the cone pulley may be connected to the base column. A first end of the spring may be connected to the base column, and a second end of the spring may be connected to the rotating shaft of the at least one movable pulley. The second cable may be coiled around the at least one movable pulley and the cone pulley. A first end of the second cable may be connected to the base column. The second end of the second cable may be connected to the mobile column. The second cable may be coiled around the cone pulley in a manner that a pulling force by the second end of the second cable on the mobile column may be in balance with the force by the mobile column and the components thereon to the second cable.

In some embodiments, the lifting system may include a block and tackle including one or more movable pulleys and one or more first fixed pulleys. The rotating shafts of the one or more first fixed pulleys may be connected to the base column. The rotating shafts of the one or more movable pulleys may be connected to the second end of the spring. The second cable may be coiled around the pulleys of the block and tackle and the cone pulley.

In some embodiments, the cone pulley may be driven by a second motor.

In some embodiments, the lifting system may adopt a leadscrew mechanism including a third motor, a screw rod, and a nut. The screw rod may be disposed on the base column. The third motor may be configured to drive the screw rod to rotate. The nut may be disposed on the screw. The nut may be connected to the mobile column to drive the mobile column.

In some embodiments, the lifting system may include an electric cylinder or an electro-hydraulic push rod. The electric cylinder or the electro-hydraulic push rod may be disposed on the base column. The electric cylinder or the electro-hydraulic push rod may be configured to drive the mobile column to move.

In some embodiments, the lifting system may include a spring balancer and a second fixed pulley. A housing of the spring balancer may be connected to the base column. A cable of the spring balancer may be coiled around the second fixed pulley, and an end of the cable is connected to the mobile column. A rotating shaft of the second fixed pulley may be connected to the base column.

In some embodiments, the lifting system may further include a fourth motor configured to drive the spring balancer to release or retract the cable.

In some embodiments, the supporting arm may be a telescopic arm extendable and retractable along a substantially horizontal direction relative to the base column.

In some embodiments, the object may include a radiation component for emitting radiation rays.

According to another aspect of the present disclosure, a radiation system is provided. The radiation system may include a body, a radiation component for emitting radiation rays and a lifting apparatus. The lifting apparatus may include a base column, a mobile column, a sliding component, a supporting arm, a lifting system, and a move-coordination system. The base column may be connected to the body and rotatable relative to the body with respect to a vertical axis. The mobile column may be connected to the base column and is vertically movable relative to the base column. The lifting system may be configured to cause a vertical movement of the mobile column relative to the base column. The sliding component may be connected to the mobile column and be vertically movable relative to the mobile column. The mobile column and the sliding component may be connected via the move-coordination system, which enables the sliding component to move simultaneously according to a predetermined relative motion relationship. The supporting arm may be connected to the sliding component. The supporting arm may be configured to support the radiation component.

In some embodiments, the radiation system may further include a control unit configured to control the radiation component.

In some embodiments, the body may include a chassis and a mobile component connected to the chassis. The mobile component may enable a user to move the radiation system to another location.

In some embodiments, the supporting arm may be a telescopic arm extendable and retractable relative to the sliding component along a substantially horizontal direction, thus allowing the radiation component to be moved further away or brought closer to the telescopic column along the substantially horizontal direction.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTIONS OF THE DRAWINGS

The present disclosure is further described in terms of example embodiments. These example embodiments are described in detail with reference to the drawings. These embodiments are non-limiting examples, in which like reference numerals represent similar structures throughout the several views of the drawings, and wherein.

DETAILED DESCRIPTION

Figure 1:
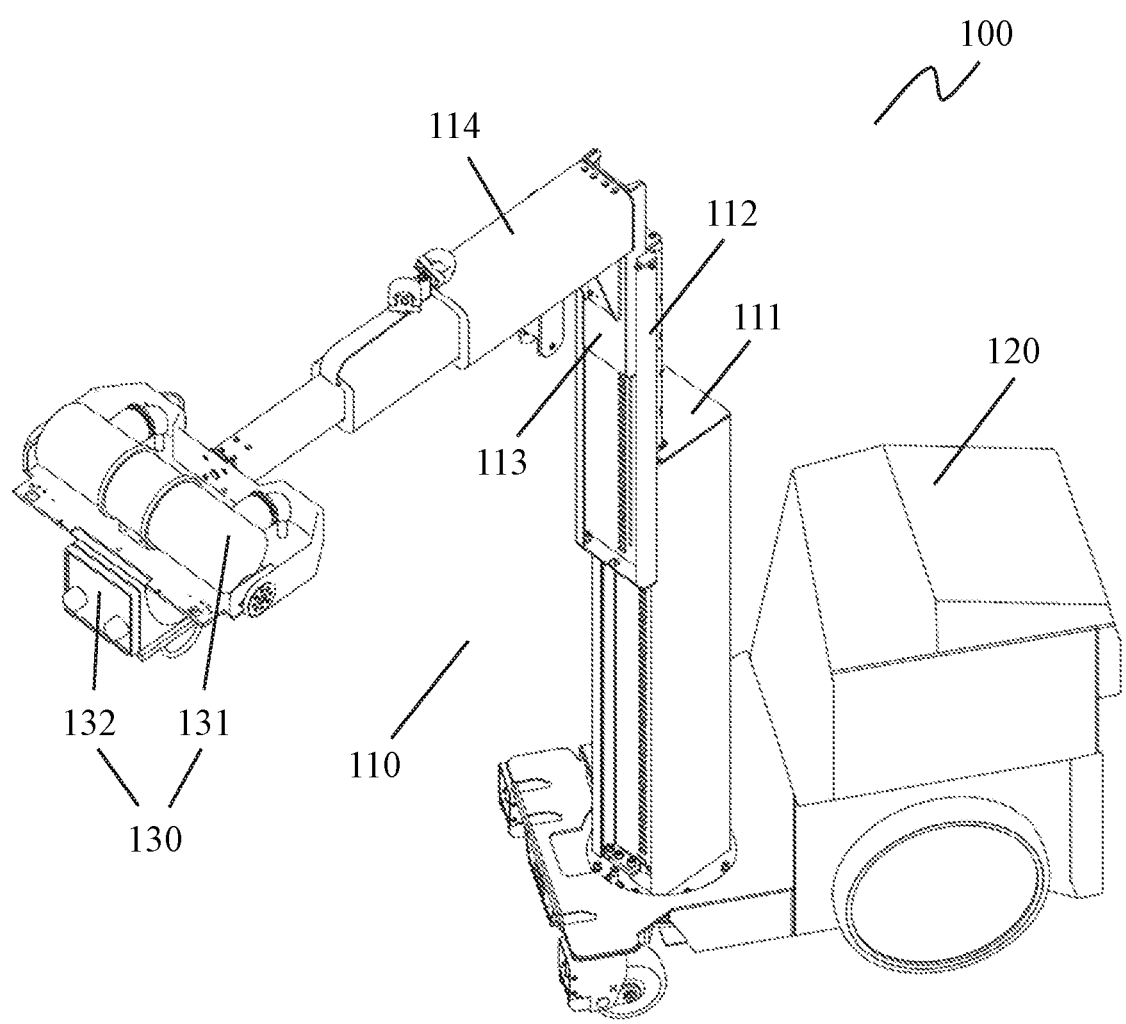
FIG. 1 is a schematic diagram illustrating a mobile radiation apparatus according to some embodiments of the present disclosure.

The present disclosure provides a lifting apparatus for lifting or lowering an object. The lifting apparatus may include a base column, a mobile column, a sliding component, a supporting arm, a lifting system, and a move-coordination system. The mobile column may be connected to the base column and is vertically movable relative to the base column. The lifting system may be configured to cause the vertical movement of the mobile column. The sliding component may be connected to the mobile column and is vertically movable relative to the mobile column. The mobile column and the sliding component are connected via the move-coordination system, which may enable the sliding component to move along with the mobile column according to a predetermined relative motion relationship. The supporting arm is connected to the sliding component and configured to support the object. The predetermined relative motion relationship may allow the sliding component and the mobile column to move along the same direction, and the moving distance of the sliding component is proportional to the moving distance of the mobile column. Such a configuration may enlarge the movement range of the object supported on the supporting arm with respect to the base column of the lifting apparatus. In some embodiments, such a lifting apparatus may be integrated into a mobile radiation apparatus and the object supported on the supporting arm may be the radiation component of the mobile radiation apparatus. The lifting apparatus may facilitate the imaging/therapy process as well as the movement of the mobile radiation apparatus. However, it is noted that the lifting apparatus may also be implemented in other application fields.

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise", "comprises", and/or "comprising", "include", "includes", and/or "including", when used in this specification, specify the presence of stated features, integers, steps, operations, elements, and/or components, but do not preclude the presence or addition of one or more other features, integers, steps, operations, elements, components, and/or groups thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements (for example, between layers) are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent").

It should also be understood that terms such as "top," "bottom," "upper," "lower," "vertical," "lateral", "longitudinal" "above," "below," "upward(s)," "downward(s)," "left," "right," and other such spatial reference terms are used in a relative sense to describe the positions or orientations of certain surfaces/parts/components of the apparatus in relationship to other such features of the apparatus when the apparatus is in a normal operating position, and may change if the position or orientation of the apparatus changes.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure.

Figure 2:
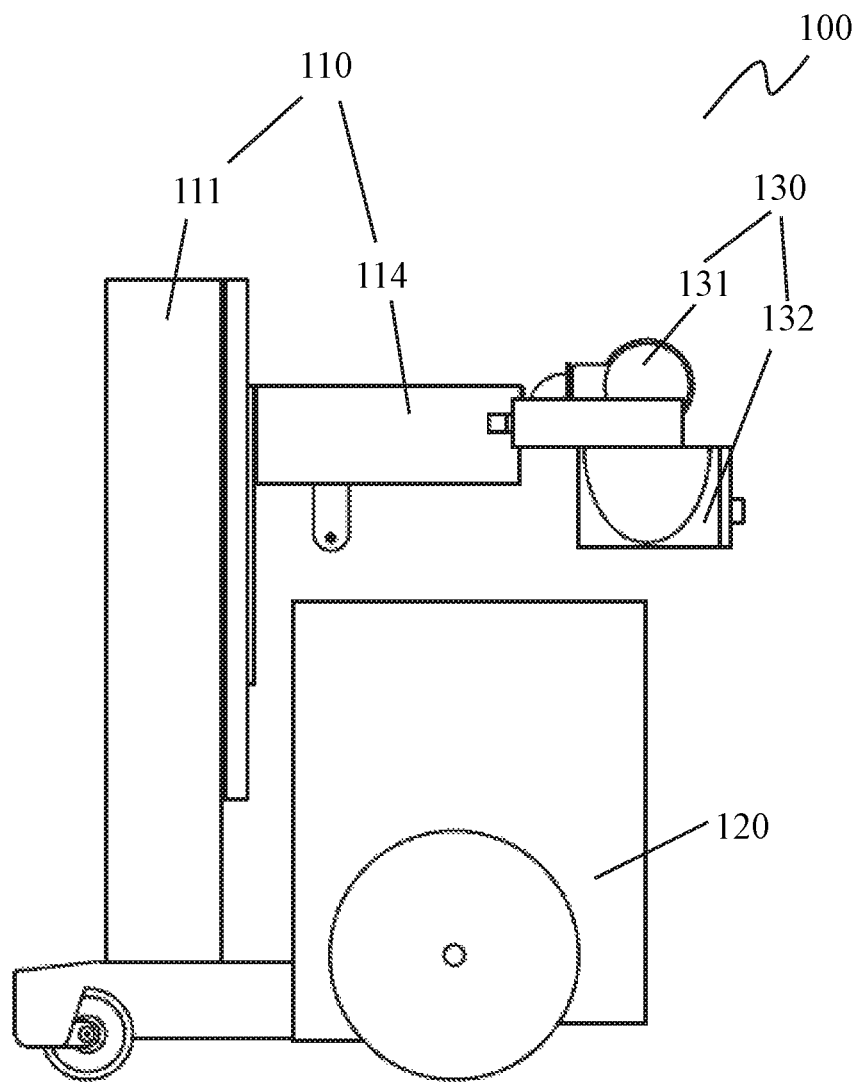
FIG. 2 is a schematic diagram illustrating a retraction state of the mobile radiation apparatus illustrated in FIG. 1 according to some embodiments of the present disclosure.

FIG. 1 is a schematic diagram illustrating a mobile radiation apparatus 100 according to some embodiments of the present disclosure. FIG. 2 is a schematic diagram illustrating a retraction state of the mobile radiation apparatus 100 illustrated in FIG. 1 according to some embodiments of the present disclosure. In some embodiments, the mobile radiation apparatus 100 may be configured to generate a medical image (e.g., an X-ray image, a computed tomography (CT) image, a positron emission computed tomography (PET) image, a magnetic resonance (MR) image, an ultrasound image), perform a radiation therapy (e.g., for treating a tumor), or the like, or any combination thereof. The mobile radiation apparatus 100 may be or include a mobile X-ray apparatus (mobile X-ray device), a mobile alpha ray apparatus, a mobile beta ray apparatus, a mobile gamma ray apparatus, a mobile proton/heavy particle accelerator, a mobile ultrasound apparatus, or the like, or any combination thereof.

In some embodiments, the mobile radiation apparatus 100 may include a lifting apparatus 110 and a body 120. Specifically, the lifting apparatus 110 may be disposed on the body 120, and the body 120 may be configured to support the lifting apparatus 110. The body 120 may include a chassis. The chassis may be disposed on the bottom of the body 120. At least one mobile component may be connected to the chassis and may enable a user to move the radiation system to another location. In some embodiments, the at least one mobile component may be or include a plurality of wheels to facilitate the movement of the mobile radiation apparatus 100. In some embodiments, the plurality of wheels (e.g., four wheels) may be universal wheels disposed on each corner of the bottom of the body 120. In some embodiments, the plurality of wheels may include one or more (e.g., one, two) universal wheels and one or more (e.g., two) fixed wheels. The one or more universal wheels may be configured to control the moving direction of the mobile radiation apparatus 100. The one or more fixed wheels may be configured to assist the movement of the mobile radiation apparatus 100. It is noted that, the at least one mobile component may take any other proper form for moving the mobile radiation apparatus 100 in different application scenarios or environments, such as wheels, robotic legs, caterpillar tracks, etc.

The lifting apparatus 110 may include a base column 111, a mobile column 112, a sliding component 113, and a supporting arm 114. The lifting apparatus 110 may be configured to lift the support arm 114. The base column 111 may be disposed on the body 120. The base column 111 may be connected to the body 120 and rotate around the body 120. In some embodiments, the base column 111 may be rotatable around a vertical axis of the body. In some embodiments, the vertical axis may be the central axis of the base column 111 or a vertical rotating shaft located at the center of the cross section of the base column 111. In some embodiments, the vertical axis may not be the central axis of the base column 111. For example, the vertical axis may be the central axis of a vertical rotating shaft that is not located at the center of the cross section of the base column 111 or even outside the base column 111. In some embodiments, the base column 111 may be connected to the body 120 through one or more machine elements such as a bearing, a turntable, or the like, or any combination thereof. In some embodiments, the base column 111 may be rotatable about the vertical axis with any reasonable angle according to actual need. For example, the base column 111 may be rotated about the vertical axis with an angle of 15°, 30°, 45°, 60°, 75°, 90°, 180°, 270°, etc. In some embodiments, the cantilever end of the supporting arm 114 may support a radiation component 130 (e.g., an X-ray emitter). Specifically, the radiation component 130 may include a tube 131 and a collimator 132. In some embodiments, the supporting arm 114 may be telescopic. For example, the supporting arm 114 may include multiple portions (or be referred to as stages) arranged in a multi-stage telescopic form, in which a first portion adjacent to a second portion may be nested within the second portion and is extended or retracted relative to the second portion. Such a configuration may allow the radiation component 130 to move along the supporting arm 114. In some embodiments, the supporting arm 114 may be extendable and retractable along a substantially horizontal direction relative to the base column 111. Correspondingly, the radiation component 130 may move along the substantially horizontal direction back and forth. As shown in FIG. 1, via the movement of the mobile radiation apparatus 100, the rotation of the base column 111 relative to the body 120, the movement of the sliding component 113 and the mobile column 112, and the extension and retraction of the supporting arm 114, the radiation component 130 may be conveniently moved to any position to facilitate the radiation imaging/therapy in different scenarios. As shown in FIG. 2, when the mobile radiation apparatus 100 is not operating or moving, it may be retracted to the retraction state to save space and avoid obscuring the sight of a mover. The process of retracting the mobile radiation apparatus 100 from an extension state (e.g., as shown in FIG. 1) to the retraction state may include retracting the supporting arm 114, lowering the mobile column 112 and rotating the base column 111 to their default positions relative to the body 120.

In some embodiments, the body 120 may include a user console (or be referred to as a control unit). The user console may be configured to control the radiation component 130 to perform a radiation imaging or a radiation therapy on a patient. In some embodiments, the user console may be configured further to control the lifting apparatus 110 and/or the at least one mobile component. For example, the user console may cause the movement of the mobile radiation apparatus 100, the rotation of the base column 111, the vertical movement of the lifting apparatus 110, and/or the extension and retraction of the supporting arm 114 by transmitting one or more control signals thereto.

It is noted that, the lifting apparatus 110 may also be adopted in application scenarios other than a mobile radiation apparatus. For example, the lifting apparatus 110 may be integrated into a fixed radiation apparatus that cannot be moved to another location and support the radiation component of the fixed radiation apparatus. As another example, the lifting apparatus 110 may be integrated into a crane configured to deliver building materials (or other objects) from a lower position to a higher position, or vice versa. The application field of the lifting apparatus 110 is not limited in the present disclosure.

Figure 3:
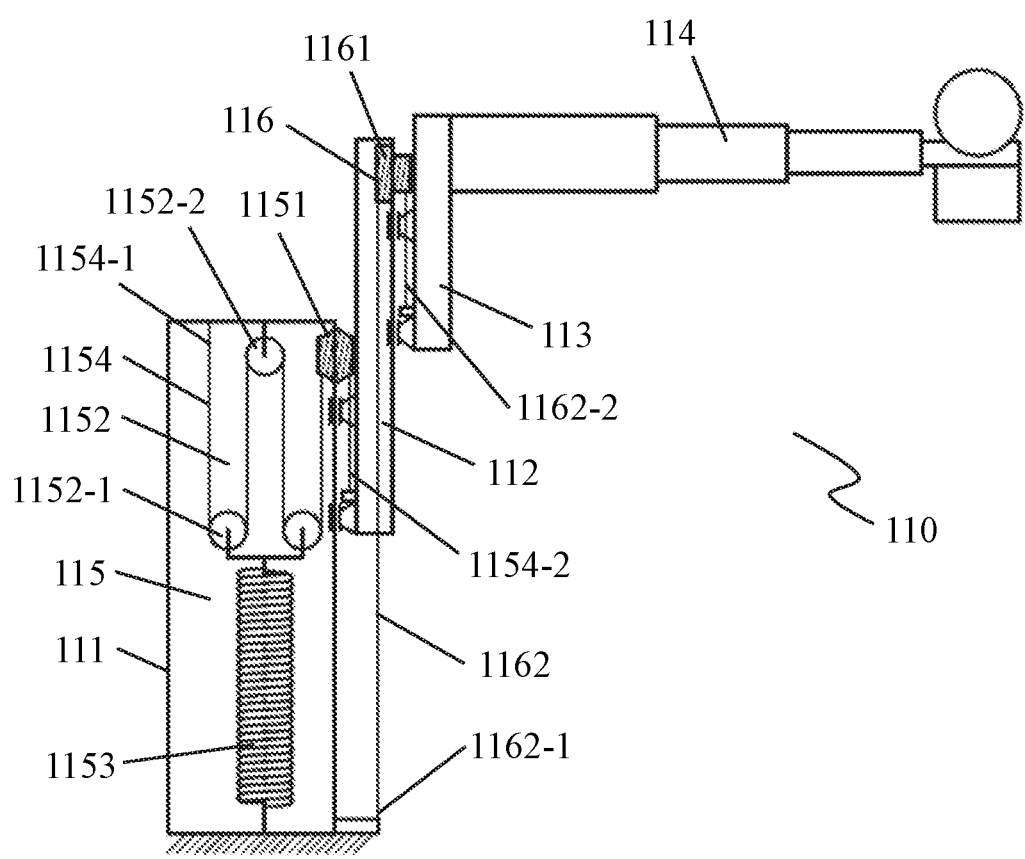
FIG. 3 is a schematic diagram illustrating a lifting apparatus of the mobile radiation apparatus illustrated in FIG. 1 according to some embodiments of the present disclosure.
Figure 4:
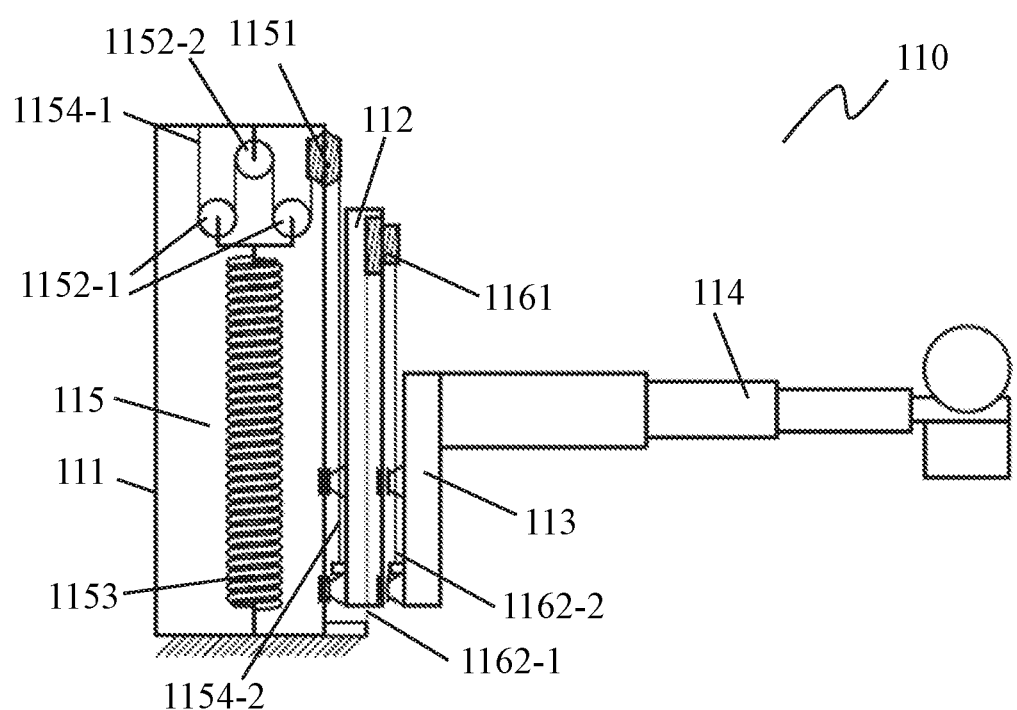
FIG. 4 is a schematic diagram illustrating the lifting apparatus illustrated in FIG. 3 in the retraction state according to some embodiments of the present disclosure.

FIG. 3 is a schematic diagram illustrating the lifting apparatus 110 of the mobile radiation apparatus 100 illustrated in FIG. 1 according to some embodiments of the present disclosure. FIG. 4 is a schematic diagram illustrating the lifting apparatus 110 illustrated in FIG. 3 in the retraction state according to some embodiments of the present disclosure. Embodiments of the lifting apparatus 110 are described in detail as following, which is merely for demonstration purposes and not intended to be limiting.

As shown in FIGS. 3 and 4, the lifting apparatus 110 may include a base column 111, a mobile column 112, a sliding component 113, and a supporting arm 114. The mobile column 112 may be connected to the base column 111 and is movable relative to the base column 111. In some embodiments, the lifting apparatus 110 may include a lifting system 115 configured to cause a vertical movement of the mobile column 112 relative to the base column 111. For example, the mobile column 112 may be connected to the base column 111 via at least one of a guide wheel, a slide rail, or the like, or any combination thereof, so as to enable the aforementioned vertical movement. The vertical movement may also be a non-zero vertical component of a sloped movement of the mobile column 112 relative to the base column 111. For example, the lifting system 115 may cause the mobile column 112 to move along a diagonal path relative to the base column 111, then the "vertical movement" may be the vertical component of such a movement.

The sliding component 113 may also be connected to the mobile column 112 (e.g., via at least one of a guide wheel, a slide rail) and is movable relative to the mobile column 112. In some embodiments, the lifting system 115 may cause the mobile column 112 to move relative to the base column 111 according to a predetermined moving pattern. For example, the lifting system 115 may cause the mobile column 112 to move a predetermined distance at a predetermined speed, within a predetermined time, and/or with a predetermined acceleration/deceleration. In some embodiments, the mobile column 112 and the sliding component 113 may be connected via a move-coordination system 116, which may enable the sliding component 113 and the mobile column 112 to move simultaneously according to a predetermined relative motion relationship. In some embodiments, the predetermined relative motion relationship may include that the sliding component 113 moves relative to the mobile column 112 and the mobile column 112 moves relative to the base column 111 both along the same direction. For example, when the mobile column 112 is moving upward relative to the basis column 111, the sliding component 113 may also move upward relative to the mobile column 112 accordingly; when the mobile column 112 is moving downward relative to the basis column 111, the sliding component 113 may also move downward relative to the mobile column 112 accordingly. As another example, when the sliding component 113 is moving upward relative to the mobile column 112, the mobile column 112 may also move upward relative to the base column 111 accordingly; when the sliding component 113 is moving downward relative to the mobile column 112, the mobile column 112 may also move downward relative to the base column 111 accordingly. The supporting arm 114 may be connected (e.g., fixed) to the sliding component 113, so that the supporting arm 114 may move along with the sliding component 113. For example, the supporting arm 114 may be connected to the sliding component 113 via bolting, welding, gluing, locking, snap-fit, or the like, or any combination thereof.

Alternatively, in some embodiments, the predetermined relative motion relationship may include that the sliding component 113 moves relative to the mobile column 112 and the mobile column 112 moves relative to the base column 111 along different directions or opposite directions. For example, when the mobile column 112 is moving upward relative to the basis column 111, the sliding component 113 may move downward relative to the mobile column 112; when the mobile column 112 is moving downward relative to the basis column 111, the sliding component 113 may move upward relative to the mobile column 112.

In some embodiments, the predetermined relative motion relationship may also include that the moving distance of the sliding component 113 relative to the mobile column 112 is proportional to the moving distance of the mobile column 112 relative to the base column 111.

It is noted that, in the present disclosure, the sliding component 113 and the mobile column 112 moving according to the predetermined relative motion relationship may represent that the direction, along which the sliding component 113 moves relative to the mobile column 112, and the direction, along which the mobile column 112 moves relative to the base column 111, are in a predetermined certain relationship. Such a configuration may allow the radiation component 130 supported on the supporting arm 114 to have a relative large and predictable moving range with respect to the base column 111. Potential accidents due to the unpredicted movement of the sliding component 113 and/or the mobile column 112 may also be reduced. In some embodiments, the above configuration may also allow (but not necessarily require) the sliding component 113 and the mobile column 112 to be driven by a single driving system with reduced amount of components, so as to reduce the weight of the lifting system 110 or the mobile radiation apparatus 100. As a result, the balance and the mobility of the mobile radiation apparatus 100 may be improved.

For example, as shown in FIGS. 3 and 4, the move-coordination system 116 may include a first pulley 1161 and a first cable 1162. A first end 1162-1 of the first cable 1162 may be connected (e.g., fixed) to the base column 111. The rotating shaft of the first pulley 1161 may be connected (e.g., fixed) to the mobile column 112. A second end 1162-2 of the first cable 1162 may be connected (e.g., fixed) to the sliding component 113 through the first pulley 1161. In some embodiments, the first pulley 1161 may be rotatable about the rotating shaft thereof. For example, the rotating shaft of the first pulley 1161 may be connected to the mobile column 112 through locking, snap-fit, bolting, or the like, or any combination thereof.

In some embodiments, the first pulley 1161 may be disposed at the top of the mobile column 112. The first end 1162-1 of the first cable 1162 may be connected (e.g., fixed) to the bottom of the base column 111. Thus, the operating of the lifting apparatus 110 may not be obstructed by the first cable 1162 and the first pulley 1161. In some embodiments, the first end 1162-1 of the first cable 1162 may be connected to another portion of the base column 111 (e.g., middle, top), which is not limited in the present disclosure. In some embodiments, the second end 1162-2 of the first cable 1162 may be connected (e.g., fixed) to the lower middle or the bottom of the sliding component 113, thereby making the first cable 1162 more easily to pull the mobile column 112 and the sliding component 113. In some embodiments, the connection between the first end 1162-1 and the base column 111 and the connection between the second end 1162-2 and the sliding component 113 may be or may include welding, locking, snap-fit, fastening, or the like, or any combination thereof.

In some embodiments, the first cable 1162 may include one or more high-strength materials (e.g., a metal such as steel, an alloy, a ceramic material, carbon fibers, glass fibers) to ensure that the lifting apparatus 110 can normally operate.

In some embodiments, the first cable 1162 may also be replaced by two cables with suitable lengths, which may be respectively connected or fixed (e.g., fixed via locking snap-fit, fastening, tying) to the first pulley 1161, coiled around different portions the first pulley 1161, so that the lifting apparatus 110 can normally operate. For example, one of the two cables may coil around a portion of the first pulley 1161 that is closer to the mobile column 112. The other one of the two cables may coil around a portion of the first pulley 1161 that is closer to the sliding component 113.

In some embodiments, a groove may be disposed on the outer surface of the first pulley 1161, and the first cable 1162 may coil around the first pulley 1161 in the groove, so that the movement of lifting and lowering the sliding component 113 along with the components thereon may be smooth.

In some embodiments, a safety locking mechanism may be disposed between the mobile column 112 and the base column 111, and/or, between the sliding component 113 and the mobile column 112 to prevent the mobile column 112 and/or the sliding component 113 from falling when the first cable 1162 is broken. For example, the safety locking mechanism may be or include an electrically magnetic attachment mechanism (such as an electromagnet). For example, the electrically magnetic attachment mechanism may include an attaching end and a magnet end that can electromagnetically attract to each other, attaching together. The attaching end may include an electromagnet, and the magnet end may include a permanent magnet or one or more ferromagnetic materials (e.g., Fe or an alloy thereof). The attaching end and the magnet end may be respectively disposed on the mobile column 112 and the base column 111, and/or be respectively disposed on the sliding component 113 and the mobile column 112. For example, the attaching end may be mounted on the mobile column 112, and the magnet end may be mounted on the base column 111. For example, when a locking is in need (e.g., when a falling of the mobile column 112 or a broken of the first cable 1162 is detected), the electrically magnetic attachment mechanism may be powered to generate an electromagnetically attractive force between the attaching end and the magnet end, thereby causing the mobile column 112 to be attached to the base column 111 to prevent the falling. It is also possible that the magnetic end is mounted on the sliding component 113, and the magnet end is mounted on the mobile column 112.

In some embodiments, the safety locking mechanism may be disposed on the first pulley 1161. For example, the attaching end may be mounted on the mobile column 112, and the magnet end may be disposed on the first pulley 1161 (e.g., the first pulley 1161 itself may also serve as the magnet end). When a locking is in need, the electrically controlled magnetic structure may be powered to generate an electromagnetically attractive force between the mobile column 112 and the first pulley 1161 to block the rotation of the first pulley 1161.

In some embodiments, the safety locking mechanism may include or be in connection with one or more detectors (e.g., sensors). The one or more detectors may be configured to detect whether the first cable 1162 is broken or whether the mobile column 112 is falling. For example, the one or more detectors may include a tension sensor, e.g., disposed on the mobile column 112, the sliding component 113, or the base column 111. The tension sensor may be connected to the first cable 1162 and configured to detect the tension of the first cable 1162. When the detected tension of the first cable 1162 is smaller than a predetermined value (e.g., zero), the cable may be determined as broken. As another example, the one or more detectors may include a speed sensor, e.g., disposed on the mobile column 112, the sliding component 113, the supporting arm 114, or the radiation component 130. The speed sensor may be configured to detect the speed of the mobile column 112, the sliding component 113, and/or the radiation component 130. When the detected speed is larger than a predetermined value, the mobile column 112 may be determined as being falling. When the one or more detectors detect that the cable is broken or the mobile column 112 is falling, it may transmit a control signal to a controller that controls the safety locking mechanism. In response to the control signal, the controller may cause the safety locking mechanism to operate to stop the falling of the mobile column 112.

In some embodiments, the safety locking mechanism may include multiple attracting ends and corresponding magnetic ends to enhance the locking performance.

In some embodiments, the first pulley 1161 may be a pulley with a uniform radius (or be referred to as a single-radius pulley), i.e., the radius of a portion of the first pulley 1161 that is closer to the mobile column 112 may be equal to the radius of a portion of the first pulley 1161 that is closer to the sliding component 113. In some embodiments, the first pulley 1161 may be a multi-radii pulley such as a two-radii pulley. For example, the radius of a portion of the first pulley 1161 that is closer to the mobile column 112 may be different from the radius of a portion of the first pulley 1161 that is closer to the sliding component 113. In these cases, when the first pulley 1161 is a single-radius pulley, through the move-coordination system 116, the moving distance (or speed) of the mobile column 112 relative to the base column 111 may be equal to the moving distance (or speed) of the sliding component 113 relative to the mobile column 112. In other words, the moving distance (or speed) of the sliding component 113 relative to the base column 111 is twice the moving distance (or speed) of the mobile column 112 relative to the base column 111. In these cases, when the first pulley 1161 is a multi-radii pulley such as a two-radii pulley, the ratio of the moving distance (or speed) of the mobile column 112 relative to the base column 111 to the moving distance (or speed) of the sliding component 113 relative to mobile column 112 may be adjusted by adjusting the ratio of the two radius of the two-radii pulley. (In other words, the ratio of the moving distance (or speed) of the mobile column 112 relative to the base column 111 to the moving distance (or speed) of the sliding component 113 relative to mobile column 112 may be adjusted by adjusting the ratio of the two radius of the two-radii pulley). For example, the moving distance (or speed) of the mobile column 112 relative to the base column 111 may be configured as being larger than the moving distance (or speed) of the sliding component 113 relative to the mobile column 112.

In some embodiments, the ratio of the two radius of the two-radii pulley may be equal to the ratio of the moving range of the mobile column 112 relative to the base column 111 (e.g., the maximum moving distance) to the moving range of the sliding component 113 relative to the mobile column 112. For example, assuming that the radius of the portion of the first pulley 1161 that is closer to the mobile column 112 is D, and the radius of the portion of the first pulley 1161 that is closer to the sliding component 113 is d. The moving range of the mobile column 112 relative to the base column 111 is $S_1$, and the moving range of the sliding component 113 relative to the mobile column 112 is $S_2$. The relationship between D, d, $S_1$ and $S_2$ may be expressed by:

$$D/d=S_1/S_2. \quad \text{Formula (1)}$$

The moving range $S_3$ of the sliding component 113 relative to the base column 111 may be determined by:

$$S_3=S_1+S_2. \quad \text{Formula (2)}$$

When the mobile column 112 is lifted to the highest position (or lowered to the lowest position) relative to the base column 111, the sliding component 113 may also be lifted to the highest position (or lowered to the lowest position) relative to the mobile column 112. Consequently, the total vertical moving range of the supporting arm 114 as well as the radiation component 130 may be remarkably increased in a given time period.

In some embodiments, the lifting apparatus 110 may also include a first motor. The first motor may be connected to and configured to drive the move-coordination system 116. For example, the first motor may control the movement of the sliding component 113 and/or the mobile column 112 by driving the rotation of the first pulley 1161 in the move-coordination system 116. In some embodiments, the lifting apparatus 110 may also include a controller in communication with the first motor to control the operation of the first motor, so as to move the sliding component 113 to a predetermined position. For example, according to the predetermined position and current position of the sliding component 113, the controller may determine a moving distance for moving the sliding component 113. Based on the determined moving distance, the controller may control the direction of the rotation, a power-on time, and/or the current passing through the first motor, thereby moving the sliding component 113 to the predetermined position. In some embodiments, the lifting apparatus 110 may also include a locking mechanism (such as the aforementioned safety locking mechanism). The locking mechanism may include a first state and a second state. In the first state (e.g., the unlocked state), the locking mechanism may unlock at least one element of the move-coordination system 116 (e.g., the first pulley 1161 and/or the first cable 1162) to enable the sliding component 113 to move. In the second state (e.g., the locked state), the locking mechanism may lock and keep locking the at least one element of the move-coordination system 116 (e.g., the first pulley 1161 and/or the first cable 1162) to stop and/or disable the sliding component 113 from moving. For example, when the sliding component 113 accidentally moves or falls (e.g., detected by the aforementioned one or more detectors), the locking mechanism may stop the falling of the sliding component 113. As another example, when the radiation component 130 is operating and is required to be still, the locking mechanism may also lock the at least one element to avoid potential accidents and damage.

In some embodiments, the locking mechanism may be or may include an electrically magnetic attachment mechanism (such as an electromagnet) that may prevent the first pulley 1161 from rotating by electromagnetically attaching the first pulley 1161. Alternatively or additionally, the locking mechanism may be or include any other reasonable mechanism known in the art for stopping or disabling the rotation of the first pulley 1161, such as a friction mechanism, a blocking mechanism, or the like, or any combination thereof.

In some embodiments, the lifting system 115 may include a cone pulley 1151, at least one movable pulley 1152-1, a spring 1153, and a second cable 1154. The rotating shaft of the cone pulley 1151 may be connected (e.g., fixed) to the base column 111. The cone pulley 1151 may rotate about the rotating shaft thereof. For example, the rotating shaft of the cone pulley 1151 may be connected to the base column 111 through locking, snap-fit, bolting, or the like, or any combination thereof. One end of the spring 1153 may be connected (e.g., fixed via locking or welding) to the base column 111, and the other end of the spring 1153 may be connected (e.g., fixed) to the at least one movable pulley 1152-1. In some embodiments, a plurality of grooves may be disposed on the outer surface of the cone pulley 1151 to accommodate and constrain the second cable 1154 coiled on the cone pulley 1151. The second cable 1154 may coil around the at least one movable pulley 1152-1 and the cone pulley 1151. For example, a first end 1154-1 of the second cable 1154 may be connected (e.g., fixed) to the base column 111, and a second end 1154-2 of the second cable 1154 may be connected (e.g., fixed) to the mobile column 112. The connection between the second cable 1154 and the base column 111 and/or the connection between the second cable 1154 and the mobile column 112 may be a connection via locking, snap-fit, gluing, fastening, tying, or the like. In some embodiments, by presetting the diameter/radius variation and the grooves of the cone pulley 1151 and coiling the second cable 1154 around the cone pulley 1151 with a preset trajectory, the mobile column 112 and the components (e.g., the sliding component 113, the support arm 114, etc.) thereon may be smoothly moved relative to the base column 111. For example, the coiling diameters of the second cable 1154 at different positions on the cone pulley 1151 may be different, and may match the variation of the elastic force of the spring 1153 and/or the deformation (e.g., extension, compression) of the spring 1153 (The elastic force is equal to the product of the elastic coefficient of the spring 1153 and the extent of the deformation of the spring 1153. For a given spring, the elastic coefficient is a constant. Therefore, the elastic force is proportional to the deformation). Thus, considering the variation of the elastic force, the moments of the second cable 1154 on both sides of the cone pulley may be maintained the same. In some embodiments, the second cable 1154 may coil around the cone pulley 1151 in a manner that the pulling force by the second cable 1154 on the mobile column 112 (e.g., caused by the pulling force of the spring 1153) is in balance with the force by the mobile column 112 and the components (e.g., the sliding component 113, the support arm 114) thereon to the second cable 1154 (e.g., caused by the gravity forces of the mobile column 112 and the components thereon), so that during the moving, the mobile column 112 with the components thereon may be maintained in a force-balance state and the mobile column 112 can be stopped at any position. For example, the pulling force of the second end 1154-2 of the second cable 1154 to the mobile column 112 may be equal to the sum of the gravity forces of the mobile column 112 and the components thereon and the pulling force applied by the first end 1162-1 of the first cable 1162 to the mobile column 112. Assuming that the radius of the portion of the first pulley 1161 that is closer the mobile column 112 is D, the radius of the portion of the first pulley 1161 that is closer to the sliding component 113 is d, the gravity force of the mobile column 112 is $G_1$, and the gravity force of the sliding component 113 with the components thereon is $G_2$. Then the pulling force applied by the second end 1154-2 of the second cable 1154 to the mobile column 112 may be expressed as:

$$F = G_1 + \frac{D+d}{D} \cdot G_2. \quad \text{Formula (3)}$$

In some embodiments, as shown in FIGS. 3 and 4, the spring 1153 may be a tension spring. In some embodiments, the spring 1153 may also be other elastic components. For example, the spring 1153 may also be a gas spring, an air spring, a compression spring, a mainspring, or the like, or any combination thereof. In some embodiments, the second cable 1154 may be an inextensible cable. For example, the second cable 1154 for pulling the mobile column 112 and the components thereon may include one or more high-strength materials, such as a metal such as steel, an alloy, a ceramic material, carbon fibers, glass fibers).

In some embodiments, the lifting system 115 may include a block and tackle 1152. The block and tackle 1152 may include one or more movable pulleys 1152-1 and one or more fixed pulleys 1152-2. The rotating shafts of the one or more fixed pulleys (first fixed pulley) 1152-2 may be connected (e.g., fixed) to the base column 111, and the one or more movable pulleys 1152-1 may be connected (e.g., fixed) to the spring 1153. The second cable 1154 may coil around the pulleys of the block and tackle 1152 and the cone pulley 1151. In some embodiments, the rotating shafts of the one or more fixed pulleys 1152-2 may be connected to the top of the base column 111. For example, the rotating shafts of the one or more fixed pulleys 1152-2 may be connected to the top of the base column 111 via one or more cables or one or more fittings. In some embodiments, the one or more movable pulleys 1152-1 may include one more pulley than the one or more fixed pulleys 1152-2. For example, as shown in FIG. 3 and FIG. 4, the lifting apparatus 110 may include one fixed pulley 1152-2 and two movable pulleys 1152-1. However, the number of the fixed pulley(s) 1152-2 and the number of the movable pulley(s) 1152-1 may be set according to actual needs. The block and tackle 1152 may reduce the deformation of the spring 153, so as to prevent the damage to the spring 153 caused by excessive deformation. In some embodiments, the lifting apparatus 110 may be manually operated by an operator. For example, the operator may manually push or press the mobile column 112 to vertically move the mobile column 112 upward or downward relative to the base column 111. Then the move-coordination system 116 may cause the sliding component 113 to move vertically relative to the mobile column 112. In some embodiments, the lifting apparatus 110 may include one or more manually moving mechanisms (e.g., handles, holes, slots) to facilitate the operator to lift or lower the mobile column 112 and the sliding component 113. For example, the one or more manually moving mechanisms may be disposed on the mobile column 112, the sliding component 113, the supporting arm 114, etc. In some embodiments, a pair of manually moving mechanisms (e.g., handles) may be symmetrically disposed on both sides of the mobile column 112 or the sliding component 113. In some embodiments, one or more manually moving mechanisms may be disposed at the bottom/top of the supporting arm 114. In some embodiments, one or more manually moving mechanisms may be disposed at the middle of the mobile column 112.

Figure 5:
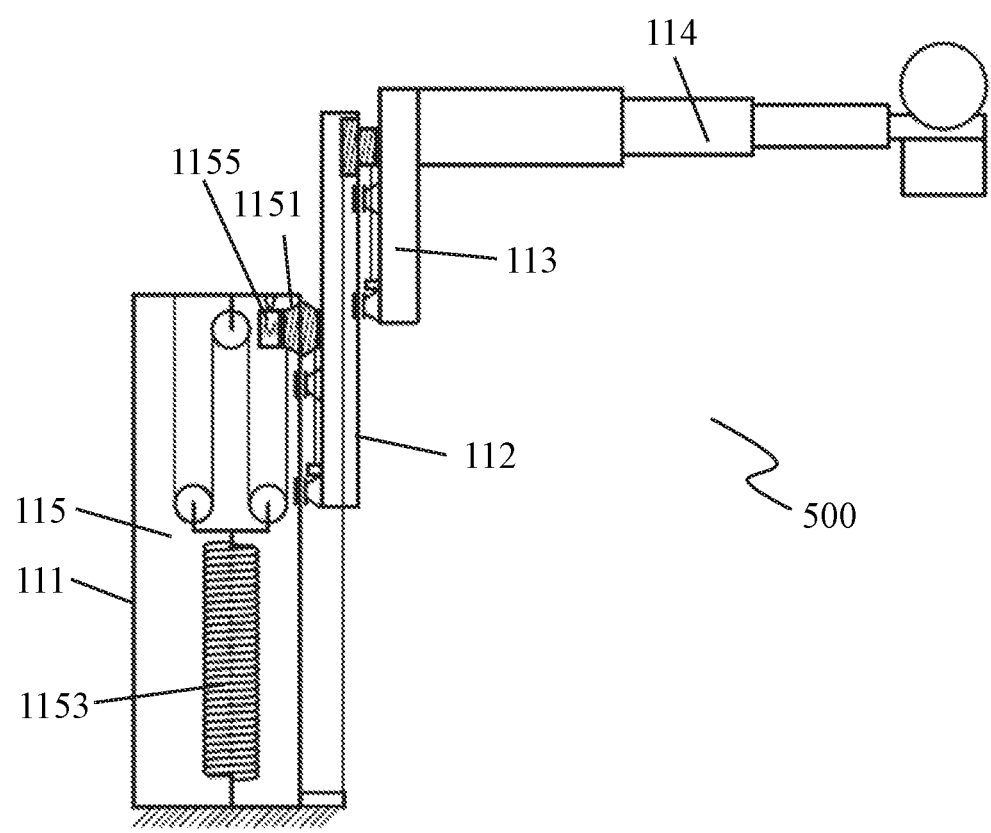
FIG. 5 is a schematic diagram illustrating an electric lifting apparatus according to some embodiments of the present disclosure.

FIG. 5 is a schematic diagram illustrating an electric lifting apparatus 500 according to some embodiments of the present disclosure. The lifting apparatus 500 may be an example of the lifting apparatus 110. Compared to the lifting apparatus 110, the lifting apparatus 500 may further include a second motor connect to the lifting system 115 and is configured to drive the lifting system 115. As shown in FIG. 5, the cone pulley 1151 may be driven by the second motor (e.g., a cone pulley motor 1155) to enable the mobile column 112 to be electrically moved relative to the base column 111. For example, the shaft of the cone pulley motor 1155 may be directly connected to the rotating shaft of the cone pulley 1151. As another example, the shaft of the cone pulley motor 1155 may be indirectly connected to the rotating shaft of the cone pulley 1151 via, e.g., a driving system. In some embodiments, the driving system may adopt at least one of a magnetic coupled driving mechanism, a hydraulic driving mechanism, a pneumatic driving mechanism, an electromechanical driving mechanism, a mechanical driving mechanism, or the like, or a combination thereof. When the cone pulley motor 1155 is powered on, the shaft of the cone pulley motor 1155 may start to rotate, which may further drive the cone pulley 1151 to rotate. The movement of the mobile column 112 may cause the sliding component 113 to move along the direction of the movement of the mobile column 112. When the mobile column 112 is moving upward, the gravitational potential energy of the mobile column 112 and the components thereon (e.g., the sliding component 113, the support arm 114) may decrease and the elastic potential energy of the spring 1153 may increase. When the mobile column 112 is moving downward, the elastic potential energy of the spring 1153 may decrease and the gravitational potential energy of the mobile column 112 and the components thereon may increase. By using the spring 1153 as the energy storage apparatus, the cone pulley motor 1155 may operate more efficiently to move the mobile column 112 upward and downward. In some embodiments, the cone pulley motor 1155 may be a variable frequency motor, a gear motor, a servo motor, or the like. In some embodiments, as shown in FIG. 5, the mobile column 112 may be electrically moved relative to the base column 111 by the second motor, or be moved manually by an operator (for example, the operator may manually push or press the mobile column 112). In some embodiments, the lifting apparatus 150 may further include a controller in communication with the second motor (e.g., cone pulley motor 1155) to control the second motor and to move the sliding component 113 to a predetermined position. In some embodiments, the lifting apparatus 115 may also include a locking mechanism. The locking mechanism may include a first state and a second state. In the first state (e.g., the unlocked state), the locking mechanism may unlock at least one element of the lifting system 115 (e.g., the cone pulley 1151) to enable the sliding component 113 to move. In the second state (e.g., the locked state), the locking mechanism may lock and keep locking the at least one element of the lifting system 115 to stop and/or disable the sliding component 113 from moving. In some embodiments, the locking mechanism may be or may include an electrically magnetic attachment mechanism (such as an electromagnet) that may prevent the cone pulley 1151 from rotating by electromagnetically attaching the cone pulley 1151. Alternatively or additionally, the locking mechanism may be or include any other reasonable mechanism known in the art for stopping or disabling the rotation of the first pulley 1161, such as a friction mechanism, a blocking mechanism, or the like, or any combination thereof.

In some embodiments, the second cable 1154 may also be pulled or coiled by manually rotating the cone pulley 1151, so as to manual move the mobile column 112 and the components (e.g., the sliding component 113, the support arm 114) thereon. For example, a handle may be connected to the shaft of the cone pulley 1151 to allow an operator to manually rotate the cone pulley 1151. As another example, a handle may be disposed outside to the base column 111 and be connected to the shaft of the cone pulley via a transmission system (e.g., a universal transmission system, a gearing transmission system, a belt drive system) to drive the cone pulley 1151.

Figure 6:
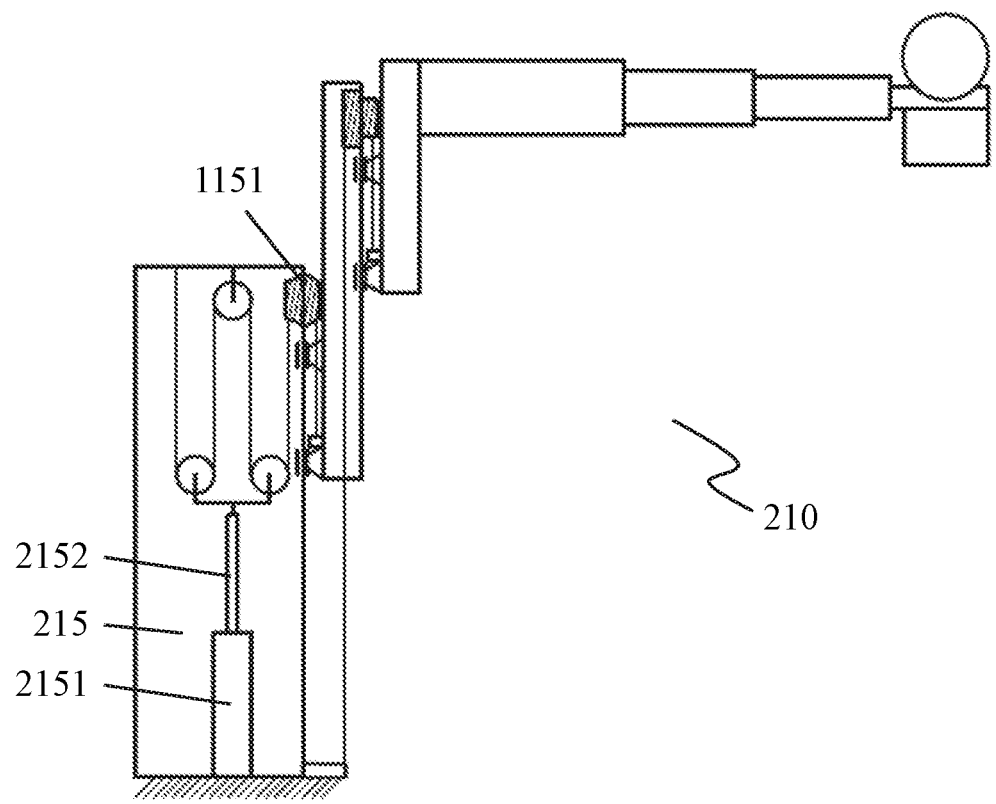
FIG. 6 is a schematic diagram illustrating a lifting apparatus according to some embodiments of the present disclosure.
Figure 7:
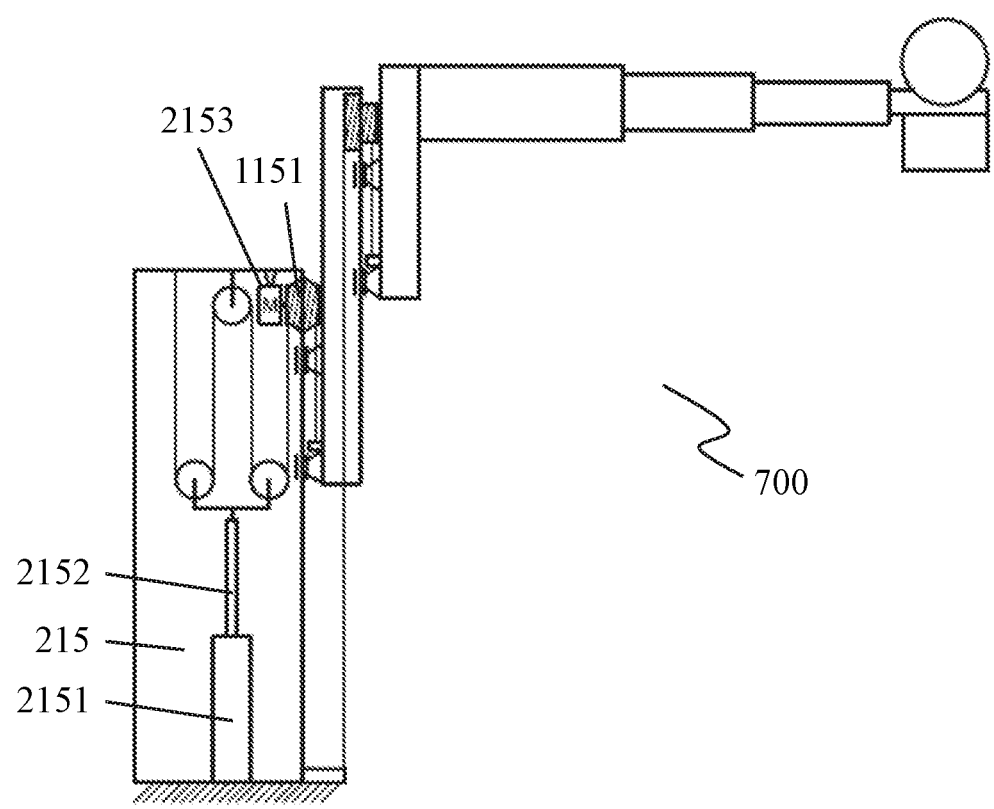
FIG. 7 is a schematic diagram illustrating an electric lifting apparatus according to some embodiments of the present disclosure.
Figure 8:
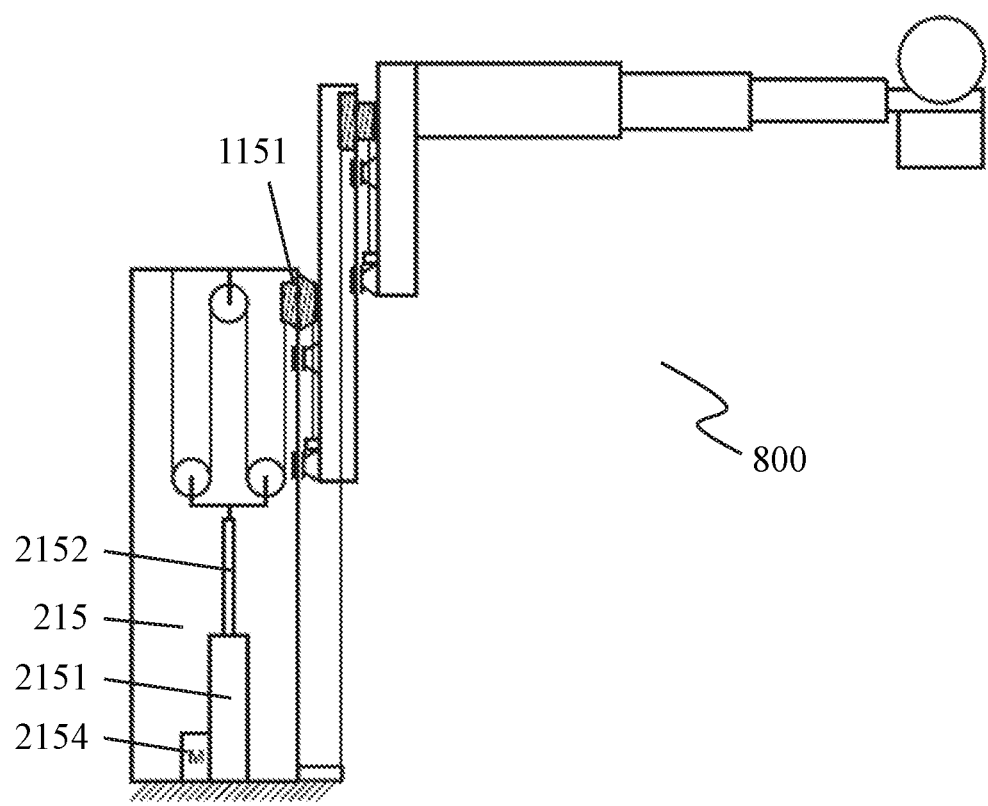
FIG. 8 is a schematic diagram illustrating an electric lifting apparatus according to some embodiments of the present disclosure.

FIG. 6 is a schematic diagram illustrating a lifting apparatus 210 according to some embodiments of the present disclosure. FIG. 7 is a schematic diagram illustrating an electric lifting apparatus 700 according to some embodiments of the present disclosure. FIG. 8 is a schematic diagram illustrating an electric lifting apparatus 800 according to still another embodiment of the present disclosure. The lifting apparatus 700 and the lifting apparatus 800 are examples of the lifting apparatus 210.

Compared to the lifting apparatus 110 shown in FIG. 3 and FIG. 4, as shown in FIG. 6, the lifting apparatus 210 may include a gas spring 215 instead of the spring 1153. By using the gas spring 215, the lifting process of the lifting apparatus 110 may be smoother and more reliable, and the service life of the lifting apparatus 110 may be extended. For example, the gas spring 215 may include a pressure cylinder 2151 and a piston rod 2152. As shown in FIG. 6, the pressure cylinder 2151 may be connected (e.g., fixed) to the base column 111. The piston rod 2152 may be connected to the rotating shafts of the one or more movable pulleys 1152-1. In some embodiments, the lifting apparatus 210 as shown in FIG. 6 may be manually operated by the operator.

In some embodiments, the lifting apparatus 210 may also be electrically operated by a driving mechanism, such as a motor. In some embodiments, as shown in FIG. 7, compared to the lifting apparatus 210 as shown in FIG. 6, the lifting apparatus 700 may further include a motor (e.g., a cone pulley motor 2153) to drive the cone pulley 1151. For example, the cone pulley motor 2153 may be a variable frequency motor, a gear motor, a servo motor, or the like, or any combination thereof. In some embodiments, as shown in FIG. 8, compared to the lifting apparatus 210 as shown in FIG. 6, the lifting apparatus 800 may further include a motor (e.g., a gas spring motor 2154) for driving the gas spring 215. For example, the gas spring 215 may be an electric gas spring. In some embodiments, under the driving of the gas spring motor 2154, the pressure in the pressure cylinder 2151 of the gas spring 215 may change, thereby causing a change of the pulling force of the gas spring 215 to control the movement of the mobile column 112 and the components (e.g., the sliding component 113, the support arm 114) thereon. For example, an electric piston may be disposed in the pressure cylinder 215. The electric piston may be driven by the motor. The pressure in the pressure cylinder 215 (e.g., the pressure between the piston rod 2152 and the electric piston) may vary with the movement of the electric piston. When the pulling force of the gas spring 215 is increased, the mobile column 112 and the components thereon may be pulled up. When the pulling force of the gas spring 215 is decreased, the mobile column 112 and the components thereon may be lowered down due to the gravity force. In some embodiments, the electric gas spring may also take any other form in the art, which is not limited in the present disclosure.

Figure 9:
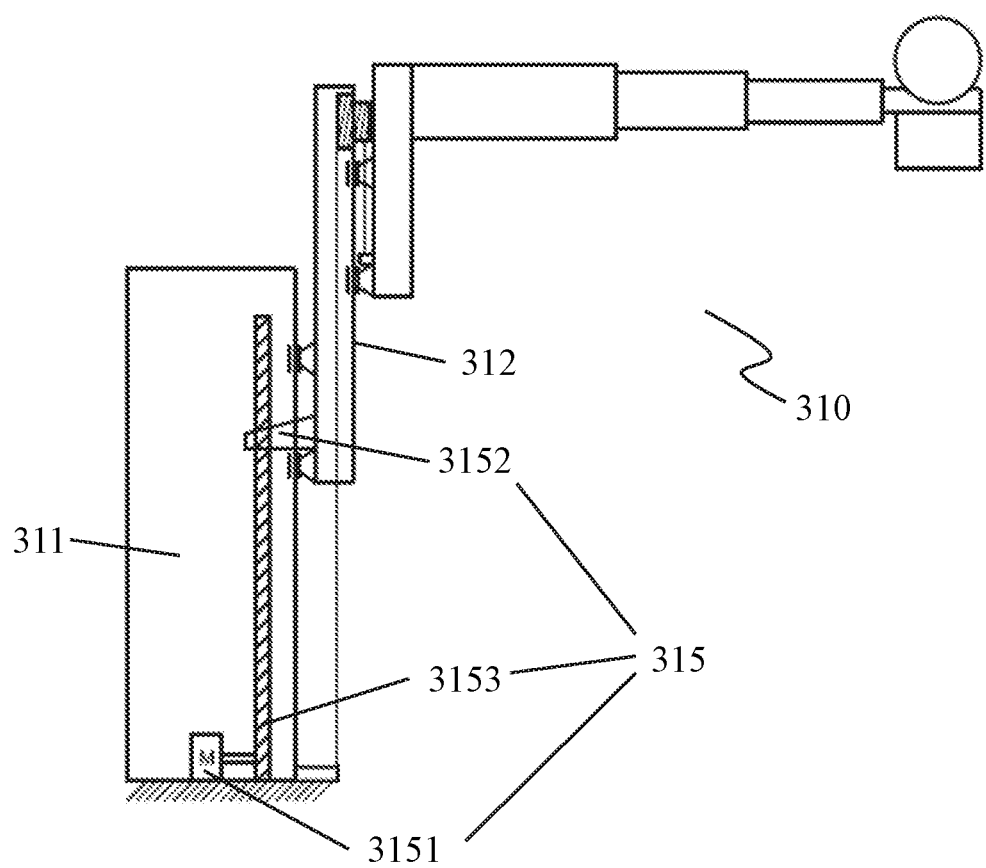
FIG. 9 is a schematic diagram illustrating an electric lifting apparatus according to some embodiments of the present disclosure.

FIG. 9 is a schematic diagram illustrating an electric lifting apparatus 310 according to some embodiments of the present disclosure. In some embodiment, as shown in FIG. 9, the lifting system 115 may be or include a leadscrew mechanism 315. For example, the leadscrew mechanism 315 may include a screw motor 3151, a screw rod 3153, and a nut 3152. The screw rod 3153 may be disposed on the base column 311. The screw motor 3151 may be configured to drive the screw rod 3153 to rotate. The nut 3152 may be disposed on the screw rod 3153 and cooperated with the screw rod 3153. The nut 3152 may be connected to the mobile column 312 to drive the mobile column 312 to move. In some embodiments, the screw rod 3153 may be a trapezoidal lead screw, a ball screw, or the like, or any combination thereof. The screw rod 3153 may be connected to the base column 311 (e.g., the bottom of the base column) via bearings and rotatable relative to the base column 311. In some embodiments, the screw motor 3151 may include a variable frequency motor, a gear motor, a servo motor, or the like, or any combination thereof. The screw motor 3151 may rotate forward and/or backward. The screw motor 3151 may drive the screw rod 3153 to rotate about its axis via a gear transmission, a belt drive, a chain drive, a wire drive, or the like, or a combination thereof. In some embodiments, the nut 3152 may be connected (e.g., fixed) to the mobile column 312 via welding, gluing, locking, snap-fit, or the like, or a combination thereof. In some embodiments, the nut 3152 and the mobile column 312 may also be integrated into one component. In some embodiments, as shown in FIG. 9, the screw motor 3151 may drive the screw rod 3153 to rotate, and the rotation of the screw rod 3153 may cause the nut 3152 to move vertically, thereby driving the mobile column 312 to move upward or downward.

In some embodiments, the lifting system 115 may also include a motor-controlled lifting mechanism such as an electric cylinder (e.g., a servo electric cylinder) or an electro-hydraulic push rod. Similar to the leadscrew mechanism 315 as shown in FIG. 9, the electric cylinder, the electro-hydraulic push rod, or another proper mechanism, may be disposed (e.g., fixed) on the base column 311. The electric cylinder or the electro-hydraulic push rod may be directly connected to the mobile column 312 and drive (e.g., push) the mobile column 312 to move.

Figure 10:
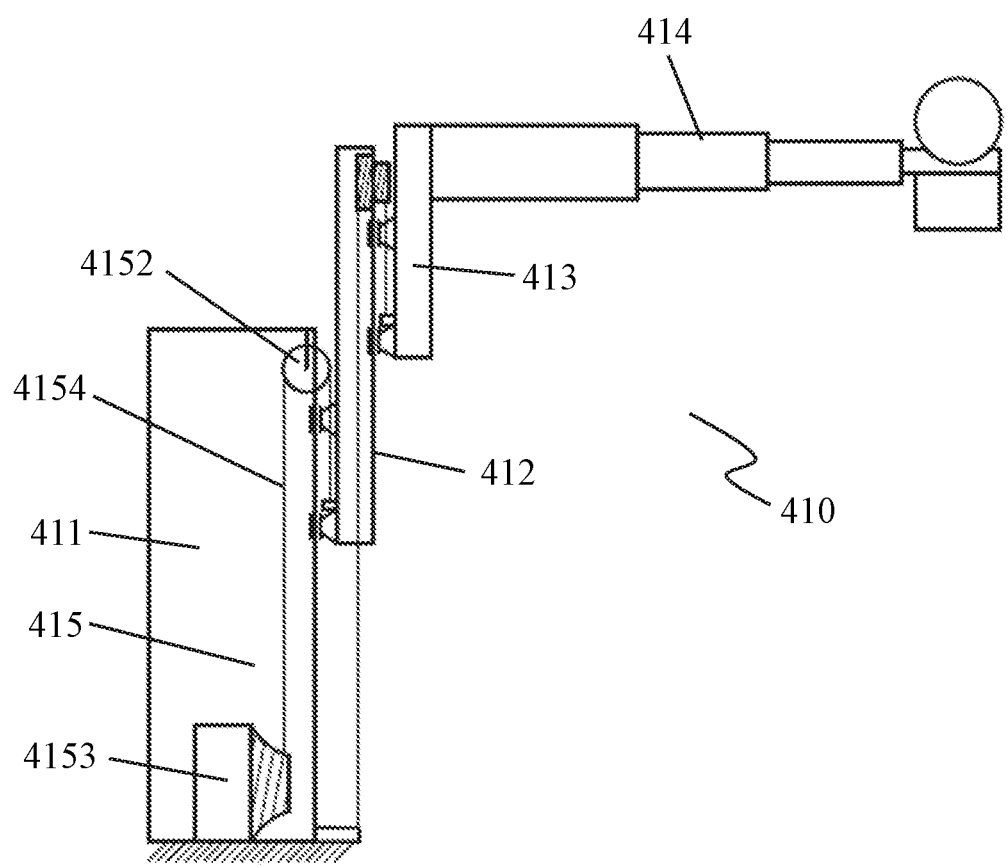
FIG. 10 is a schematic diagram illustrating a lifting apparatus according to still some embodiments of the present disclosure.
Figure 11:
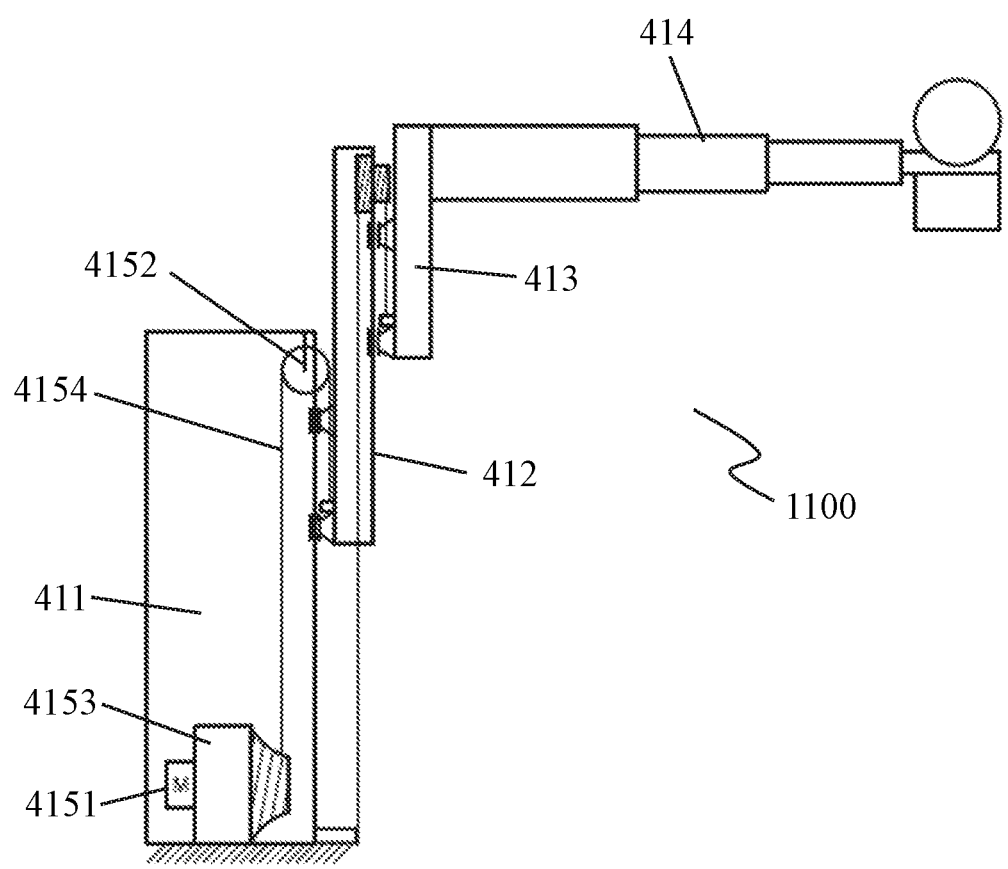
FIG. 11 is a schematic diagram illustrating an electric lifting apparatus according to some embodiments of the present disclosure.

FIG. 10 is a schematic diagram illustrating a lifting apparatus 410 according to some embodiments of the present disclosure. FIG. 11 is a schematic diagram illustrating an electric lifting apparatus 1100 according to another embodiment of the present disclosure. The lifting apparatus 1100 may be an example of the lifting apparatus 410. In some embodiments, as shown in FIG. 10 and FIG. 11, the lifting system 415 may include a spring balancer 4153 and a fixed pulley 4152 (second fixed pulley). The housing of the spring balance 4153 may be connected (e.g., fixed) to the base column 411. The cable of the spring balancer 4153 may be connected (e.g., fixed) to the mobile column 412 through the fixed pulley 4152. For example, the cable may coil around the fixed pulley 4152 and an end of the cable (the cable end 4154) may be connected to the mobile column 412. The rotating shaft of the fixed pulley 4152 may be connected (e.g., fixed) to the base column 411. In some embodiments, the spring balancer 4153 may be connected to the base column 411 via bolting, locking, snap-fit, or the like, or any combination thereof. In some embodiments, the cable end 4154 of the spring balancer may be connected to the mobile column 412 via locking, snap-fit, fastening, tying, or the like, or any combination thereof. In some embodiments, the cable end 4154 may be connected to the lower middle or bottom of the mobile column 412 so that the mobile column 112 may be better pulled. In some embodiments, the cable of the spring balancer 4153 may include one or more high-strength material, such as a metal, an alloy (e.g., steel), a ceramic material, carbon fibers, glass fibers, or the like, or any combination thereof. The lifting apparatus 410 as shown in FIG. 10 may be manually operated by an operator.

As shown in FIG. 11, compared to the lifting system 415, the lifting system 1100 may further include a motor (e.g., a spring balancer motor 4151) that is configured to drive the spring balancer 4153 to release or retract the cable. In some embodiments, the spring balancer motor 4151 may change the pulling force of the spring balancer 4153 by rotating forward or backward to release or retract the cable, thereby driving the mobile column 412 to move upward or downward relative to the base column 411. The sliding component 413 (and the supporting arm 414 thereon) may also move along the direction of the movement of the mobile column 412. In some embodiments, the spring balancer motor 4151 may be a variable frequency motor, a servo motor, or any other motor that can rotate forward and backward, which is not limited herein.

Having thus described the basic concepts, it may be rather apparent to those skilled in the art after reading this detailed disclosure that the foregoing detailed disclosure may be intended to be presented by way of example only and may be not limiting. Various alterations, improvements, and modifications may occur and are intended to those skilled in the art, though not expressly stated herein. These alterations, improvements, and modifications are intended to be suggested by this disclosure, and are within the spirit and scope of the embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment may be included in at least one embodiment of the present disclosure. Therefore, it may be emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that may be not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Furthermore, the recited order of processing elements or sequences, or the use of numbers, letters, or other designations therefore, may be not intended to limit the claimed processes and methods to any order except as may be specified in the claims. Although the above disclosure discusses through various examples what may be currently considered to be a variety of useful embodiments of the disclosure, it may be to be understood that such detail may be solely for that purposes, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purposes of streamlining the disclosure aiding in the understanding of one or more of the various inventive embodiments. This method of disclosure, however, may be not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or pcablerties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired pcablerties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein may be hereby incorporated herein by this reference in its entirety for all purposes, excepting any prosecution file history associated with same, any of same that may be inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

We claim:

1. A lifting apparatus, comprising a base column, a mobile column, a sliding component, a supporting arm, a lifting system, and a move-coordination system, wherein:
   the mobile column connected to the base column is vertically movable relative to the base column;
   the lifting system is configured to cause the movement of the mobile column;
   the sliding component connected to the mobile column is vertically movable relative to the mobile column;
   the mobile column and the sliding component are connected via the move-coordination system, which enables the sliding component and the mobile column to move simultaneously according to a predetermined relative motion relationship;
   the supporting arm is connected to the sliding component;
   the move-coordination system includes a first pulley and a first cable coiled around the first pulley, wherein the first pulley is a multi-radii pulley having a first radius and a second radius;
   a first end of the first cable is connected to the base column;
   a rotating shaft of the first pulley is connected to the mobile column; and
   a second end of the first cable is connected to the sliding component through the first pulley.

2. The lifting apparatus of claim 1, wherein the predetermined relative motion relationship includes that:
   the sliding component moves relative to the base column and the mobile column moves relative to the sliding component both along a same direction; and
   a moving distance of the sliding component relative to the mobile column is proportional to a moving distance of the mobile column relative to the base column.

3. The lifting apparatus of claim 1, wherein the first pulley is a two-radii pulley.

4. The lifting apparatus according to claim 3, wherein a ratio of the first radius to the second radius is equal to a ratio of a vertical movement distance of the mobile column relative to the base column to a vertical movement distance of the sliding component relative to the mobile column.

5. The lifting apparatus of claim 1 wherein the lifting system is configured to cause the mobile column to move relative to the base column according to a predetermined moving manner.

6. The lifting apparatus of claim 1, further comprising:

a first motor connected to and drive the move-coordination system.

7. The lifting apparatus of claim 6, further comprising:
a first controller in communication with the first motor, wherein the first controller is configured to cause the first motor to move the sliding component to a predetermined position.

8. The lifting apparatus of claim 1, further comprising:
a locking mechanism having a first state and a second state, wherein,
in the first state, the locking mechanism unlocks at least one element of the move-coordination system or the lifting system to enable the sliding component to move, and
in the second state, the locking mechanism locks the at least one element of the move-coordination system or at least one element of the lifting system to stop/disable the sliding component from moving.

9. The lifting apparatus of claim 1, wherein:
the lifting system includes a cone pulley, at least one movable pulley, a spring and a second cable;
a rotating shaft of the cone pulley is connected to the base column;
a first end of the spring is connected to the base column, and a second end of the spring is connected to the rotating shaft of the at least one movable pulley;
the second cable is coiled around the at least one movable pulley and the cone pulley, wherein a first end of the second cable is connected to the base column, and the second end of the second cable is connected to the mobile column; and
the second cable is coiled around the cone pulley in a manner that a pulling force by the second end of the second cable on the mobile column is in balance with the force by the mobile column and the components thereon to the second cable.

10. The lifting apparatus of claim 9, wherein:
the lifting system includes a block and tackle including one or more movable pulleys and one or more first fixed pulleys;
the rotating shafts of the one or more first fixed pulleys are connected to the base column;
the rotating shafts of the one or more movable pulleys are connected to the second end of the spring; and
the second cable is coiled around the pulleys of the block and tackle and the cone pulley.

11. The lifting apparatus of claim 9, wherein the cone pulley is driven by a second motor.

12. The lifting apparatus of claim 1, wherein:
the lifting system adopts a leadscrew mechanism, which includes a third motor, a screw rod, and a nut;
the screw rod is disposed on the base column, and the third motor is configured to drive the screw rod to rotate;
the nut is disposed on the screw; and
the nut is connected to the mobile column to drive the mobile column.

13. The lifting apparatus of claim 1, wherein:
the lifting system includes an electric cylinder or an electro-hydraulic push rod;
the electric cylinder or the electro-hydraulic push rod is disposed on the base column; and
the electric cylinder or the electro-hydraulic push rod is configured to drive the mobile column to move.

14. The lifting apparatus of claim 1, wherein:
the lifting system includes a spring balancer and a second fixed pulley;
a housing of the spring balancer is connected to the base column;
a cable of the spring balancer is coiled around the second fixed pulley, and an end of the cable is connected to the mobile column; and
a rotating shaft of the second fixed pulley is connected to the base column.

15. The lifting apparatus of claim 14, wherein the lifting system further includes a fourth motor configured to drive the spring balancer to release or retract the cable.

16. The lifting apparatus of claim 1, wherein the supporting arm is a telescopic arm extendable and retractable along a substantially horizontal direction relative to the base column.

17. The lifting apparatus of claim 1, wherein the supporting arm is configured to support an object, and the object includes a radiation component for emitting radiation rays.

18. A radiation system, comprising:
a body;
a radiation component for emitting radiation rays; and
a lifting apparatus, comprising a base column, a mobile column, a sliding component, a supporting arm, a lifting system, and a move-coordination system, wherein:
the base column is connected to the body and rotatable relative to the body with respect to a vertical axis;
the mobile column is connected to the base column and is vertically movable relative to the base column;
the lifting system is configured to cause a vertical movement of the mobile column relative to the base column;
the sliding component is connected to the mobile column and is vertically movable relative to the mobile column;
the mobile column and the sliding component are connected via the move-coordination system, which enables the sliding component and the mobile column to move simultaneously according to a predetermined relative motion relationship; and
the supporting arm is connected to the sliding component, wherein the supporting arm is configured to support the radiation component;
the move-coordination system includes a first pulley and a first cable coiled around the first pulley, wherein the first pulley is a multi-radii pulley having a first radius and a second radius;
a first end of the first cable is connected to the base column;
a rotating shaft of the first pulley is connected to the mobile column; and
a second end of the first cable is connected to the sliding component through the first pulley.

19. The radiation system of claim 18, further comprising:
a control unit configured to control the radiation component.

20. The radiation system of claim 18, wherein:
the body include a chassis and a mobile component connected to the chassis; and
the mobile component enables a user to move the radiation system to another location.

21. The radiation system of claim 18, wherein the supporting arm is a telescopic arm extendable and retractable relative to the sliding component along a substantially horizontal direction, thus allowing the radiation component to be moved further away or brought closer to the base column along the substantially horizontal direction.

* * * * *